(12) United States Patent
Filion et al.

(10) Patent No.: US 7,087,586 B2
(45) Date of Patent: Aug. 8, 2006

(54) OLIGONUCLEOTIDE COMPOSITIONS AND THEIR USE TO INDUCE DIFFERENTIATION OF CELLS

(75) Inventors: Mario C. Filion, Laval (CA); Nigel C. Phillips, Pointe-Claire (CA)

(73) Assignee: Bioniche Life Sciences, Inc., Belleville (CA)

( * ) Notice: Subject to any disclaimer, the term of this patent is extended or adjusted under 35 U.S.C. 154(b) by 314 days.

(21) Appl. No.: 10/127,645

(22) Filed: Apr. 22, 2002

(65) Prior Publication Data

US 2003/0045493 A1    Mar. 6, 2003

Related U.S. Application Data

(60) Provisional application No. 60/286,158, filed on Apr. 24, 2001.

(51) Int. Cl.
*A01N 43/04* (2006.01)

(52) U.S. Cl. ........................................... 514/44
(58) Field of Classification Search ................ 514/44
See application file for complete search history.

(56) References Cited

U.S. PATENT DOCUMENTS 5,851,984 A * 12/1998 Matthews et al. ............. 514/2
5,866,332 A *  2/1999 Cocks et al. ................... 435/6
5,994,320 A * 11/1999 Low et al. ..................... 514/44

OTHER PUBLICATIONS

Adunyah, S.E. et al., "Regulation of c-jun mRNA expression by hydroxyurea in human K562 cells during erythroid differentiation", Biochim. Biphys. Acta, vol. 1263, pp. 123-132, 1995.
Bates, P.J. et al., "Antiproliferative activity of G-rich oligonucleotides correlates with protein binding" J. Biol. Chem., vol. 274, No. 37, pp. 26369-26377, 1999.
Beran, M. et al., "Growth of sensitive and drug-resistant human myeloid leukemia cells in SCID mice", Hematol. Pathol., vol. 8, No. 4, pp. 135-154, 1994.
Bianchi, N. et al., "Induction of erythroid differentiation of human K562 cells by cisplatin analogs", Biochem. Pharmacol., vol. 60, No. 1, pp. 31-40, 2000.

Bianchi, N. et al., "The DNA-binding drugs mithramycin and chromomycin are powerful inducers of erythroid differentiation of human K562 cells", Br. J. Haematol., vol. 104, No. 2, pp. 258-265, 1999.
Bianchi Scarra, G.L., et al., "Terminal erythroid differentiation in the K-562 cell line by 1-beta-D-arabinofuranosylcytosine: accompaniment by c-myc messenger RNA decrease", Cancer Res, vol. 46, pp. 6327-6332, 1986.
Brem, H. et al., "Interstitial Chemotherapy with drug polymer implants for the treatment of recurrent gliomas," J. Neurosurg., vol. 74, pp. 441-446, 1991.
Cartron, J.P., "Defining the Rh Blood Group antigens, Biochemistry and molecular genetics", Blood Rev., vol. 8, Issue 4, pp. 199-212, 1994.
Cortesi, R. et al., "Human leukemic K562 cells treated with cytosine arabinoside: enhancement of erythroid differentiation by retinoic acid and retinol", Eur J Haematol, vol. 61, No. 1, pp. 295-301, 1998.
Decker, T. et al., "Immunostimulatory CpG-oligonucleotides cause proliferation, cytokine production, and an immunogenic phenotype in chronic lymphocytic leukemia B cells", Blood, vol. 95, No. 3, pp. 999-1006, 2000.
Daniels, G. and Green, C., "Expression of red cell surface antigens during erythropoiesis", Vox Sang, vol. 78 (suppl. 2), pp. 149-153, 2000.

(Continued)

*Primary Examiner*—Joseph Woltach
(74) *Attorney, Agent, or Firm*—Kilpatrick Stockton LLP

(57) ABSTRACT

The present invention provides compositions comprising a 3'-OH, 5'-OH, chemically unmodified, synthetic phosphodiester nucleotide sequence selected from the group consisting of SEQ ID NO: 1, SEQ ID NO: 2, SEQ ID NO: 3, and SEQ ID NO: 4, and a pharmaceutically acceptable carrier, wherein the compositions are useful to induce differentiation of cells or to stimulate differentiation or production of pluripotent cells. The present invention provides methods of using these compositions to induce differentiation of pluripotent cells, including bone marrow derived cells, and to treat disease associated with insufficient differentiation of cells in animals and humans, including but not limited to leukemia, lymphoma, non-malignant blood disorders such as hemoglobinopathies, sickle cell disease, myelodysplastic syndrome, pancytopenia, anemia, thrombocytopenia and leukopenia.

13 Claims, No Drawings

OTHER PUBLICATIONS

Drexler, H.G., "Leukemia cell lines: in vitro models for the study of chronic myeloid leukemia," Leuk. Res., vol. 18, issue 12, pp. 919-927, 1994.

DSMZ Catalogue of Human and Animal Cell Lines, 6th ed., Braunschweig, Germany: DSMZ 1997.

Gambari, R. et al., "Human leukemic K562 cells: suppression of hemoglobin accumulation by a monoclonal antibody to human transferring receptor", Biochem. Biophys. Acta, vol. 886, No. 1, pp. 203-213, 1986.

Gambari, R. et al., "Efficient cell proliferation and predominant accumulation of epsilon-globin mRNA in human leukemic K562 cells which produce mostly Hb Gower 1", Experientia, vol. 41, pp. 673-675, 1985.

Gruel, Y. et al., "Determination of platelet antigens and glycoproteins in the human fetus", Blood, vol. 68, No. 2, pp. 488-492, 1986.

Iyamu, E.W. et al., "Trimidox-mediated morphological changes during erythroid differentiation is associated with the stimulation of hemoglobin and F-cell production in human K562 cells", Biochem. Biophys. Res. Commun., vol. 247, No. 3, pp. 759-764, 1998.

Morassutti, C. et al., "Effect of oligomer length and base substitutions on the cytotoxic activity and specific nuclear protein recognition of GTn oligonucleotides in the human leukemic CCRF-CEM cell line", Nucleosides & Nucleotides, vol. 18, No. 6-7, pp. 1711-1716, 1999.

Osti, F. et al., "Human leukemia K562 cells: induction to erythroid differentiation by guanine, guanosine and guanine nucleotides", Haematologica, vol. 82, pp. 395-401, 1997.

Rutherford, T.R. et al., "K562 human leukaemic cells synthesise embryonic haemoglobin in response to haemin", Nature, vol. 280, pp. 164-165, 1979.

Scaggiante, B. et al., "Human cancer cell lines growth inhibition by GTn oligodeoxyribonucleotides recognizing single-stranded DNA-binding proteins", Eur. J. Biochem, vol. 252, No. 2, pp. 207-215, 1998.

Schwenke, K. et a., "Induction of differentiation in erythroleukemic K562 cells by gamma-irradiation", Leuk. Res., vol. 19, No. 12, pp. 955-961, 1995.

Tidd, D.M., et al., "Oligodeoxynucleotide 5mers containing a 5'-CpG induce apoptosis through a mitochondrial mechanism in T lymphocytic leukaemia cells", Nucleic Acids Res., vol. 28, No. 11, pp. 2242-2250, 2000.

Vlassov, V.V. et al. "Transport of oligonucleotides across natural and model membranes" Biochem. Biophys. Acta, vol. 1197, No. 2, pp. 95-108, 1994.

Wagner, R.W., "Gene inhibition using antisense oligodeoxynucleotides", Nature, vol. 372, No. 6504, pp. 333-335, 1994.

Wheater, et al., "Functional Histology, a text and color atlas", 2d ed. Churchill Livingstone UK, Blood, pp. 57-58, 1987.

Wright, S.D. et al., "CD14, a receptor for complexes of lipopolysaccharide (LPS) and LPS binding protein", Science, vol. 249, Issue 4975, pp. 1431-1433, 1990.

* cited by examiner

OLIGONUCLEOTIDE COMPOSITIONS AND THEIR USE TO INDUCE DIFFERENTIATION OF CELLS

PRIOR RELATED APPLICATIONS

The present application claims priority to U.S. provisional patent application Ser. No. 60/286,158 filed Apr. 24, 2001.

FIELD OF THE INVENTION

The present invention provides compositions comprising specific oligonucleotides combined with a pharmaceutically acceptable carrier, wherein the compositions are useful to induce differentiation of cells, including pluripotent cells, leukemic cells, lymphoma cells and bone marrow-derived cells, and to treat diseases such as leukemia, lymphoma and disorders associated with insufficient differentiation of cells.

BACKGROUND OF THE INVENTION

Numerous diseases and conditions in animals and humans are associated with insufficient differentiation of cells or with an insufficiency of cells. Many of these cells are derived from bone marrow. Such diseases and conditions include but are not limited to leukemia, lymphoma, and non-malignant blood disorders such as hemoglobinopathies, sickle cell disease, myelodysplastic syndrome and insufficient production of bone marrow derived cells following therapies such as radiation and chemotherapy.

Differentiation therapy of leukemia cells in diseases such as acute promyelocytic leukemia (APL), acute myeloid leukemia (AML), chronic promyelocytic leukemia (CPL) and chronic myeloid leukemia (CML), has provided an alternative strategy for the treatment of leukemia. In differentiation therapy, immature leukemia cells are induced by different chemical compounds to attain a mature phenotype resulting in arrest of their growth.

A number of differentiation compounds and also radiation have been reported to induce the differentiation of leukemia cells. Hemin, butyric acid, 5-azacytidine, cytosine arabinoside, hydroxyurea, guanosine, guanine, retinoic acid, trimidox, gamma-irradiation, mithramycin and chromomycin have been reported to induce differentiation of leukemia cells (Rutherford et al., Nature 280:164, 1979; Gambari et al., Biochem. Biophys. Acta, 886:203, 1986; Bianchi et al., Cancer Res. 46:6327, 1986; Adunyah et al., Biochem. Biophys. Acta, 1263:123, 1995; Osti et al., Haematologica 82:395, 1997; Cortesi et al., Eur. J. Haematol. 61:295, 1998; Iyamu et al., Biochem. Biophys. Res. Com. 247:759, 1998; Schwenke et al., Leuk. Res. 19:955, 1995; and Bianchi et al., Br. J. Haematol. 104:258, 1999).

Synthetic oligonucleotides are polyanionic sequences that are internalized in cells (Vlassov et al. Biochim. Biophys. Acta 1197:95, 1994). Synthetic oligonucleotides are reported to bind selectively to nucleic acids (Wagner, R. Nature: 372:333, 1994), to specific cellular proteins (Bates et al. J. Biol. Chem. 274:26369, 1999) and to specific nuclear proteins (Scaggiante et al. Eur. J. Biochem. 252:207, 1998), and to inhibit proliferation of cancer cells. Synthetic oligonucleotides have not been reported to possess differentiating activity on acute and/or chronic pro-myelocytic cells and/or myeloid leukemia cells. Synthetic phosphorothioate oligonucleotides having a CpG motif (5'purine-purine-cytosine (C)-guanine (G)-pyrimidine-pyrimidine3') have been shown to induce the proliferation of B-cell chronic lymphocytic leukemia (Decker et al., Blood 95:999, 2000). Synthetic 27 base sequences containing G and variable amounts of thymine (T), hereinafter oligonucleotide GTn, wherein n is ≧1 or ≦7 Ts (Scaggiante et al., Eur. J. Biochem. 252:207, 1998), and wherein the number of bases is >20 (Morassutti et al., Nucleosides and Nucleotides 18:1711, 1999), have been reported to inhibit growth of leukemia cells by sequence specific binding to a 45 kDa nuclear protein. In contrast, GTn sequences, wherein the total number of bases is less than 15, are reported to be inactive against these cells (Morassutti et al. Nucleosides and Nucleotides 18:1711, 1999). Chimeric methylphosphonodiester/phosphodiester oligonucleotides of sequence type CGNNN (N=A, C, G or T)), introduced into the cytoplasm of cells by 10 minutes of reversible permeabilization with streptolysin O, induce apoptosis of human T cell leukemia cells. Nevertheless, the CGNNN oligonucleotides are reported to be inactive against three CML cell lines (K562, LAMA84 and KYO1), showing no significant effect on the growth and survival of these cells (Tidd et al., Nucleic Acid Res. 28:2242, 2000).

Depletion of bone marrow derived cells is observed in several conditions, including depletion following radiation therapy or chemotherapy. Insufficient production of cells destined to become erythrocytes or granulocytes is associated with numerous problems, including but not limited to, reduced delivery of oxygen to cells, decreased immune function, and clotting abnormalities. Various therapies, including expensive chemotherapies, are often required to stimulate production of red and white cells.

Most prior art differentiating therapies have proven to be less than adequate for clinical applications. Many of these therapies are inefficient or toxic, have significant adverse effects and are debilitating for the recipient. Therefore, there is a continuing need for novel compositions and methods that induce differentiation of cells such as myeloid-derived leukemia cells. What is also needed are new therapeutic compositions and methods that stimulate production and differentiation of pluripotent cells such as bone-marrow derived cells. Also needed are new therapeutic compositions that induce differentiation of cells. What is also needed are compositions and methods that may be used to treat diseases and conditions characterized by insufficient differentiation of cells or insufficient production of marrow derived cells.

SUMMARY OF THE INVENTION

The present invention fulfills these needs by providing a method comprising administration of a composition comprising a 3'-OH, 5'-OH, chemically unmodified, synthetic phosphodiester oligonucleotide sequence (hereinafter sequence) selected from the group consisting of SEQ ID NO: 1 (5'GTG3'), SEQ ID NO: 2 (5'GGGTGG3'), SEQ ID NO: 3 (5'GGGAGG3') and SEQ ID NO: 4 (5'CCACCC3') and a pharmaceutically acceptable carrier, wherein the composition induces differentiation of cells. The present invention provides a method to treat diseases associated with growth of cells that are not differentiated to a mature phenotype. Terminal differentiation of cells may include one or more responses selected from the group consisting of induction of erythrocyte-like phenotype, monocyte-like phenotype, megakaryocyte-like phenotype, inhibition of proliferation of leukemia cells and induction of hemoglobin synthesis.

The compositions of the present invention may be used to treat diseases related to insufficient differentiation of cells. Such diseases include but are not limited to leukemia, lymphoma, and non-malignant blood disorders such as hemoglobinopathies, sickle cell disease or myelodysplastic syndrome. The compositions of the present invention are believed to be useful for treatment of pancytopenia, anemia, thrombocytopenia and leukopenia. Other conditions that may be treated with the compositions of the present invention include lymphoma and nonmalignant blood disorders, including but not limited to hemoglobinopathies, sickle cell disease and myelodysplastic syndromes. In a preferred embodiment, the compositions of the present invention are administered to an animal or a human with leukemia in an amount effective to treat the leukemia.

The compositions of the present invention may also be administered to an animal or human together with other therapies as a combination therapy. These therapies may include administration of therapeutic compounds or radiation therapy. The compositions of the present invention may be administered before, after, or concomitantly with the other therapy. Such combination therapy may augment the net therapeutic effect on the animal or human. The compositions of the present invention may be administered alone, or in combination with other therapeutic modalities including, but not limited to, chemotherapeutic agents, differentiating agents, immunotherapeutic agents, antimicrobial agents, antiviral agents or in combination with radiation therapy.

The compositions of the present invention may be administered to a recipient to stimulate production of cells after other therapies administered to the recipient have depleted such cells. One non-limiting example involves depletion of cells derived from bone marrow following radiation therapy or chemotherapy. The compositions of the present invention may also be administered to a recipient to stimulate production and differentiation of other cells such as pluripotent stem cells, myeloid stem cells, lymphoid stem cells, progenitor cells, immune cell precursors, and/or other cells derived from these pluripotent stem cells, myeloid stem cells, lymphoid stem cells, progenitor cells, and immune cell precursors. The compositions of the present invention may also be administered to a recipient to stimulate production and differentiation of cells from numerous sources, including but not limited to, bone marrow, liver, spleen, lymph nodes, thymus and cord blood.

The compositions of the present invention may also be administered in vitro to affect differentiation of cells such as pluripotent stem cells, myeloid stem cells, lymphoid stem cells, progenitor cells, immune cell precursors, and/or other cells derived from these pluripotent stem cells, myeloid stem cells, lymphoid stem cells, progenitor cells, and immune cell precursors.

The unexpected and surprising ability of the composition of the present invention to induce differentiation of bone-marrow derived cells, including leukemia cells, addresses a long-felt, unfulfilled need in the medical arts and provides an important benefit for animals and humans.

Accordingly, it is an object of the present invention to provide a method comprising administration of a composition comprising a 3'-OH, 5'-OH, chemically unmodified, synthetic phosphodiester oligonucleotide sequence (hereinafter sequence) selected from the group consisting of SEQ ID NO: 1 (5'GTG3'), SEQ ID NO: 2 (5'GGGTGG3'), SEQ ID NO: 3 (5'GGGAGG3') and SEQ ID NO: 4 (5'CCACCC3') and a pharmaceutically acceptable carrier to treat disease in animals and humans, wherein the disease is characterized by insufficient differentiation of cells.

Another object of the present invention is to provide a method comprising administration of a composition comprising a 3'-OH, 5'-OH, chemically unmodified, synthetic phosphodiester oligonucleotide sequence (hereinafter sequence) selected from the group consisting of SEQ ID NO: 1 (5'GTG3'), SEQ ID NO: 2 (5'GGGTGG3'), SEQ ID NO: 3 (5'GGGAGG3') and SEQ ID NO: 4 (5'CCACCC3') and a pharmaceutically acceptable carrier to induce progenitor cell maturation and differentiation in animals and humans.

Another object of the present invention is to provide a composition and method to treat leukemia.

Yet another object of the present invention is to provide a method that inhibits proliferation of leukemic cells and induces differentiation of leukemic cells.

Another object of the present invention is to provide a method to treat lymphoma.

Yet another object of the present invention is to provide a method to treat non-malignant blood disorders.

Still another object of the present invention is to provide a method to treat hemoglobinopathies.

A further object of the present invention is to provide a method to treat sickle cell disease.

Yet another object of the present invention is to provide a method to treat myelodysplastic syndrome.

Another object of the present invention is to provide a method to treat pancytopenia.

Yet another object of the present invention is to provide a method to treat anemia.

A further object of the present invention is to provide a method to treat thrombocytopenia.

Another object of the present invention is to provide a method to treat leukopenia.

Still another object of the present invention is to provide a method to induce progenitor cell maturation and differentiation.

Yet another object of the present invention is to provide a method to induce maturation and differentiation of cells including but not limited to pluripotent stem cells, myeloid stem cells, lymphoid stem cells, progenitor cells, immune cell precursors, and/or other cells derived from these pluripotent stem cells, myeloid stem cells, lymphoid stem cells, progenitor cells, and immune cell precursors.

Still another object of the present invention is to provide a method to induce bone marrow-derived progenitor cell maturation.

Another object of the present invention is to provide a method that increases the number of bone marrow derived-cells following treatment with therapeutic agents.

Yet another object of the present invention is to provide a method that increases the number of bone marrow derived-cells following treatment with chemotherapeutic agents.

Another object of the present invention is to provide a method that restores the number of bone marrow derived-cells following treatment with radiotherapy.

Still another object of the present invention is to provide a method that restores the number of bone marrow derived-cells following treatment with immunosuppressive agents.

Still another object of the present invention is to provide a composition that is minimally toxic to the recipient.

These and other objects, features and advantages of the present invention will become apparent after a review of the following detailed description of the disclosed embodiments and the appended claims.

DETAILED DESCRIPTION OF THE INVENTION

The present invention may be understood more readily by reference to the following detailed description of specific embodiments included herein.

The present invention comprises a method comprising administration of a composition comprising a 3'-OH, 5'-OH, chemically unmodified, synthetic phosphodiester oligonucleotide sequences (hereinafter sequence) selected from the group consisting of SEQ ID NOs: 1, 2, 3, or 4, and a pharmaceutically acceptable carrier, to an animal or a human in an amount effective to induce differentiation of cells. The compositions of the present invention may be used to treat disease related to insufficient differentiation of cells. Such diseases include but are not limited to leukemia, lymphoma, and non-malignant blood disorders such as hemoglobinopathies, sickle cell disease and myelodysplastic syndrome. The compositions of the present invention are believed to be useful for treatment of pancytopenia, anemia, thrombocytopenia and leukopenia. Other conditions that may be treated with the compositions of the present invention include lymphoma and nonmalignant blood disorders, including but not limited to hemoglobinopathies, sickle cell disease and myelodysplastic syndromes. The unexpected and surprising ability of these compositions to induce differentiation and to inhibit proliferation of leukemia cells addresses a long felt unfulfilled need in the medical arts and provides an important benefit for animals and humans.

The present invention also comprises a method comprising administration of a composition comprising a 3'-OH, 5'-OH, chemically unmodified, synthetic phosphodiester oligonucleotide sequence (hereinafter sequence) selected from the group consisting of SEQ ID NO: 1 (5'GTG3'), SEQ ID NO: 2 (5'GGGTGG3'), SEQ ID NO: 3 (5'GGGAGG3') and SEQ ID NO: 4 (5'CCACCC3') and a pharmaceutically acceptable carrier, to induce maturation of progenitor cells in animals and humans. Such cells include but are not limited to pluripotent stem cells, mycloid stem cells, lymphoid stem cells, immune cell precursors, and/or other cells derived from these pluripotent stem cells, myeloid stem cells, lymphoid stem cells and immune cell precursors. The compositions of the present invention may also be administered to an animal or human to stimulate production and differentiation of cells from numerous sources, including but not limited to, bone marrow, liver, spleen, lymph nodes, thymus and cord blood.

As used herein, the word "sequence" refers a sequence comprising a 3'-OH, 5'-OH chemically unmodified, synthetic phosphodiester nucleotide sequence selected from the group consisting of SEQ ID NO: 1 (5'GTG3'), SEQ ID NO: 2 (5'GGGTGG3'), SEQ ID NO: 3 (5'GGGAGG3') and SEQ ID NO: 4 (5'CCACCC3').

The word "response", as used herein refers to one or more of the following non-limiting examples of responses: induced differentiation of pluripotent stem cells, myeloid stem cells, lymphoid stem cells, immune cell precursors, and/or other cells derived from these pluripotent stem cells, myeloid stem cells, lymphoid stem cells and immune cell precursors; induced differentiation of erythrocyte-like cells, monocyte-like cells or megakaryocyte-like cells; inhibition of cellular proliferation due to the induction of terminal differentiation; induction of hemoglobin synthesis; and stimulation of hemoglobin synthesis.

As used herein, the phrase "effective in responsive cells" refers to the ability of the compositions of the present invention to induce differentiation and/or inhibition of proliferation and/or synthesis of hemoglobin.

As used herein, the phrases "therapeutic treatment", "effective amount" and "amount effective to" refer to an amount of a sequence effective to induce differentiation of cells, to inhibit proliferation of cells or to stimulate production of pluripotent cells such as bone marrow-derived cells.

The word "disease", as used herein, relates to a condition wherein bodily health is impaired.

As used herein, the phrase "chemotherapeutic" is any agent approved by a regulatory agency of a country or a state government or listed in the U.S. Pharmacopoeia or other generally recognized pharmacopoeia for use to treat cancer in an animal or human. As used herein, the phrase "chemotherapeutic" includes immunosuppressive agents.

Administration of an effective amount of the composition of the present invention to an animal or a human is a therapeutic treatment that prevents, treats or eliminates a disease including, but not limited to, leukemia, pancytopenia, anemia, thrombocytopenia, leukopenia, lymphoma, and non-malignant blood disorders such as hemoglobinopathies, sickle cell disease or myelodysplastic syndrome. Types of leukemia include, but are not limited to APL, AML, CPL and CML. Administration of an effective amount of the composition of the present invention to an animal or a human is also a therapeutic treatment that stimulates production of progenitor cells, including but not limited to pluripotent stem cells, myeloid stem cells, lymphoid stem cells, immune cell precursors, and/or other cells derived from these pluripotent stem cells, myeloid stem cells, lymphoid stem cells and immune cell precursors. In a preferred embodiment, the present invention provides a method to stimulate production and differentiation of marrow derived cells. The compositions of the present invention may also be administered to an animal or human to stimulate production and differentiation of cells from numerous sources, including but not limited to, bone marrow, liver, spleen, lymph nodes, thymus and cord blood.

The terms "pharmaceutically acceptable carrier" or "pharmaceutically acceptable vehicle" are used herein to mean, without limitation, any liquid, solid or semi-solid, including, but not limited to, water or saline, a gel, cream, salve, solvent, diluent, fluid ointment base, ointment, paste, implant, liposome, micelle, giant micelle, and the like, which is suitable for use in contact with living animal or human tissue without causing adverse physiological responses, and which does not interact with the other components of the composition in a deleterious manner. Other pharmaceutically acceptable carriers or vehicles known to one of skill in the art may be employed to make compositions for delivering the oligonucleotide sequences of the present invention.

The oligonucleotide sequences of the present invention may be combined with pharmaceutically acceptable carriers and administered as compositions in vitro or in vivo. Forms of administration include, but are not limited to, injections, solutions, creams, gels, implants, pumps, ointments, emulsions, suspensions, microspheres, particles, microparticles, nanoparticles, liposomes, pastes, patches, tablets, transdermal delivery devices, sprays, aerosols, or other means familiar to one of ordinary skill in the art. Such pharmaceutically acceptable carriers are commonly known to one of ordinary skill in the art. Pharmaceutical formulations of the present invention can be prepared by procedures known in the art using well known and readily available ingredients. For example, the compounds can be formulated with common excipients, diluents, or carriers, and formed into tablets, capsules, suspensions, powders, and the like. Examples of excipients, diluents, and carriers that are suitable for such formulations include the following: fillers and extenders (e.g., starch, sugars, mannitol, and silicic derivatives); binding agents (e.g., carboxymethyl cellulose and other cellulose derivatives, alginates, gelatin, and polyvinyl-pyrrolidone); moisturizing agents (e.g., glycerol); disintegrating agents (e.g., calcium carbonate and sodium bicarbonate); agents for retarding dissolution (e.g., paraffin); resorption accelerators (e.g., quaternary ammonium compounds); surface active agents (e.g., cetyl alcohol, glycerol monostearate); adsorptive carriers (e.g., kaolin and bentonite); emulsifiers; preservatives; sweeteners; stabilizers; coloring agents; perfuming agents; flavoring agents; lubricants (e.g., talc, calcium and magnesium stearate); solid polyethyl glycols; and mixtures thereof.

The formulations can be so constituted that they release the active ingredient only or preferably in a particular location, possibly over a period of time. Such combinations provide yet a further mechanism for controlling release kinetics. The coatings, envelopes, and protective matrices may be made, for example, from polymeric substances or waxes.

Compositions comprising one or more sequences and a pharmaceutically acceptable carrier are prepared by uniformly and intimately bringing into association the sequence and the pharmaceutically acceptable carrier. Pharmaceutically acceptable carriers include liquid carriers, solid carriers or both. Liquid carriers are aqueous carriers, non-aqueous carriers or both, and include, but are not limited to, aqueous suspensions, oil emulsions, water-in-oil emulsions, water-in-oil-in-water emulsions, site-specific emulsions, long-residence emulsions, sticky-emulsions, microemulsions and nanoemulsions. Solid carriers are biological carriers, chemical carriers or both and include, but are not limited to, viral vector systems, particles, microparticles, nanoparticles, microspheres, nanospheres, minipumps, bacterial cell wall extracts and biodegradable or non-biodegradable natural or synthetic polymers that allow for sustained release of the oligonucleotide compositions. Emulsions, minipumps and polymers can be implanted in the vicinity of where delivery is required (Brem et al. J. Neurosurg. 74: 441, 1991). Methods used to complex an oligonucleotide sequence(s) to a solid carrier include, but are not limited to, direct adsorption to the surface of the solid carrier, covalent coupling to the surface of the solid carrier, either directly or via a linking moiety, and covalent coupling to the polymer used to make the solid carrier. Optionally, a sequence(s) can be stabilized by the addition of non-ionic or ionic polymers such as polyoxyethylenesorbitan monooleates (TWEENs) or hyaluronic acid.

Preferred aqueous carriers include, but are not limited to, water, saline and pharmaceutically acceptable buffers. Preferred non-aqueous carriers include, but are not limited to, a mineral oil or a neutral oil including, but not limited to, a diglyceride, a triglyceride, a phospholipid, a lipid, an oil and mixtures thereof, wherein the oil contains an appropriate mix of polyunsaturated and saturated fatty acids. Examples include, but are not limited to, soybean oil, canola oil, palm oil, olive oil and myglyol, wherein the fatty acids can be saturated or unsaturated. Optionally, excipients may be included regardless of the pharmaceutically acceptable carrier used to present the oligonucleotide compositions to cells. These excipients include, but are not limited to, anti-oxidants, buffers, and bacteriostats, and may include suspending agents and thickening agents.

One or more sequences may be administered alone, or in combination with other therapeutic modalities including, but not limited to, chemotherapeutic agents, differentiating agents, immunotherapeutic agents, antimicrobial agents, antiviral agents or in combination with radiation therapy. Differentiating agents include, but are not limited to, hemin, butyric acid, 5-azacytidine, cytosine arabinoside, hydroxyurea, guanosine, guanine, retinoic acid, trimidox, gamma-irradiation, mithramycin and chromomycin. Chemotherapeutic agents include, but are not limited to, anti-metabolites, DNA damaging, microtubule destabilizing, microtubule stabilizing, actin depolymerizing, growth inhibiting, topoisomerase inhibiting, HMG-CoA inhibiting, purine inhibiting, pyrimidine inhibiting, metalloproteinase inhibiting, CDK inhibiting, angiogenesis inhibiting, differentiation enhancing and immunotherapeutic agents. Dosages and methods of administration of these other therapeutic modalities are known to one of ordinary skill in the art.

Methods of in vivo administration of the compositions of the present invention, or of formulations comprising such compositions and other materials such as carriers of the present invention that are particularly suitable for various forms include, but are not limited to the following types of administration, oral (e.g. buccal or sublingual), anal, rectal, as a suppository, topical, parenteral, aerosol, inhalation, intrathecal, intraperitoneal, intravenous, intraarterial, transdermal, intradermal, subdermal, intramuscular, intrauterine, vaginal, into a body cavity, surgical administration at the location of a tumor or internal injury, directly into tumors, into the lumen or parenchyma of an organ, and into bone marrow. Techniques useful in the various forms of administrations mentioned above include but are not limited to, topical application, ingestion, surgical administration, injections, sprays, transdermal delivery devices, osmotic pumps, electrodepositing directly on a desired site, or other means familiar to one of ordinary skill in the art. Sites of application can be external, such as on the epidermis, or internal, for example a gastric ulcer, a surgical field, or elsewhere.

The compositions of the present invention can be applied in the form of creams, gels, solutions, suspensions, liposomes, particles, or other means known to one of skill in the art of formulation and delivery of the compositions. Ultrafine particle sizes can be used for inhalation delivery of therapeutics. Some examples of appropriate formulations for subcutaneous administration include but are not limited to implants, depot, needles, capsules, and osmotic pumps. Some examples of appropriate formulations for vaginal administration include but are not limited to creams and rings. Some examples of appropriate formulations for oral administration include but are not limited to: pills, liquids, syrups, and suspensions. Some examples of appropriate formulations for transdermal administration include but are not limited to gels, creams, pastes, patches, sprays, and gels. Some examples of appropriate delivery mechanisms for subcutaneous administration include but are not limited to implants, depots, needles, capsules, and osmotic pumps. Formulations suitable for parenteral administration include but are not limited to aqueous and non-aqueous sterile injection solutions which may contain anti-oxidants, buffers, bacteriostats and solutes which render the formulation isotonic with the blood of the intended recipient, and aqueous and non-aqueous sterile suspensions which may include suspending agents and thickening agents. Extemporaneous injection solutions and suspensions may be prepared from sterile powders, granules and tablets commonly used by one of ordinary skill in the art.

Embodiments in which the compositions of the invention are combined with, for example, one or more pharmaceutically acceptable carriers or excipients may conveniently be presented in unit dosage form and may be prepared by conventional pharmaceutical techniques. Such techniques include the step of bringing into association the compositions containing the active ingredient and the pharmaceutical carrier(s) or excipient(s). In general, the formulations are prepared by uniformly and intimately bringing into association the active ingredient with liquid carriers. Preferred unit dosage formulations are those containing a dose or unit, or an appropriate fraction thereof, of the administered ingredient. It should be understood that in addition to the ingredients particularly mentioned above, formulations comprising the compositions of the present invention may include other agents commonly used by one of ordinary skill in the art.

The volume of administration will vary depending on the route of administration. Such volumes are known to one of ordinary skill in the art of administering compositions to animals or humans. Depending on the route of administration, the volume per dose is preferably about 0.001 to 100 ml per dose, more preferably about 0.01 to 50 ml per dose and most preferably about 0.1 to 30 ml per dose. For example, intramuscular injections may range in volume from about 0.1 ml to 1.0 ml. The oligonucleotide compositions administered alone, or together with other therapeutic agent(s), can be administered in a single dose treatment, in multiple dose treatments, or continuously infused on a schedule and over a period of time appropriate to the disease being treated, the condition of the recipient and the route of administration. Moreover, the other therapeutic agent can be administered before, at the same time as, or after administration of the oligonucleotide compositions.

Preferably, the amount of oligonucleotide composition administered per dose is from about 0.0001 to 100 mg/kg, more preferably from about 0.001 to 10 mg/kg and most preferably from about 0.01 to 5 mg/kg. In a preferred embodiment, the oligonucleotide compositions in combination with a chemotherapeutic agent is administered to an animal or human having leukemia in an amount effective to add to, synergize with or potentiate the anti-neoplastic effect of the chemotherapeutic agent. Preferably, the amount of therapeutic agent administered per dose is from about 0.001 to 1000 mg/kg, more preferably from about 0.01 to 500 mg/kg and most preferably from about 0.1 to 100 mg/kg. The particular sequence and the particular therapeutic agent administered, the amount per dose, the dose schedule and the route of administration should be decided by the practitioner using methods known to those skilled in the art and will depend on the type of disease, the severity of the disease, the location of the disease and other clinical factors such as the size, weight and physical condition of the recipient. In addition, in vitro assays may optionally be employed to help identify optimal ranges for sequence and for sequence plus therapeutic agent administration.

The compositions of the present invention may also be administered in vitro to affect differentiation of cells such as pluripotent stem cells, myeloid stem cells, lymphoid stem cells, progenitor cells, immune cell precursors, and/or other cells derived from these pluripotent stem cells, myeloid stem cells, lymphoid stem cells, progenitor cells, and immune cell precursors.

The present invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention.

EXAMPLE 1

Preparation of Sequences

Phosphodiester nucleotide sequences (SEQ ID NOs: 1, 2, 3 and 4) were prepared by Sigma-Genosys (Woodlands, Tex.) using Abacus Segmented Synthesis Technology. Unless stated otherwise, the sequences were dispersed in autoclaved deionized water or in a pharmaceutically acceptable buffer such as, but not limited to, saline immediately prior to use.

EXAMPLE 2

Cells

The K562 cell line derived from the leukemic cells of a CML patient in blastic crisis is used as the standard model for determining, in vitro, the therapeutic potential of new differentiating compounds (Rutherford et al., Nature, 280: 164, 1979; Drexler et al. DSMZ Catalogue of Human and Animal Cell Lines, $6^{th}$ ed., Braunschweig, Germany: DSMZ, 1997). K562 cells were obtained from the American Type Culture Collection (ATCC, Rockville, Md.) and were cultured in the medium recommended by the ATCC.

EXAMPLE 3

Hemoglobin Synthesis by K562 Cells Cultured with SEQ ID NO: 1, SEQ ID NO: 2, SEQ ID NO: 3 and SEQ ID NO: 4.

K562 cells were seeded in 1.0 ml at $2.0 \times 10^5$ cells/ml in 6-well flat-bottomed tissue culture plates for 72 hours with 100 µg of SEQ ID NO: 1, SEQ ID NO: 2, SEQ ID NO: 3 or SEQ ID NO: 4. For hemoglobin determination, the cells were washed twice by centrifugation in phosphate-buffered saline (PBS), stained with 0.2% benzidine (Sigma-Aldrich Canada, Oakville, Ontario) in 0.5 M acetic acid activated with 10% $H_2O_2$ (Gambari et al., Experimentia 41:673, 1985). After 10 minutes incubation in the dark, the percentages of benzidine positive cells (hemoglobin positive cells) were determined by light microscopy using an hemocytometer. Approximately 500 cells were counted for the determination of the percentages of benzidine positive cells. Cell size was also determined by light microscopy. Hemin (20 µg) was added to K562 cells for 72 hours as a control for hemoglobin synthesis. Hemin was obtained from Sigma-Aldrich Canada.

TABLE 1

Evaluation of hemoglobin synthesis (benzidine-positivity) and cell size of K562 cells

| SEQUENCE | % of benzidine-positive cells | Cell size |
| --- | --- | --- |
| None | 5.4 | normal |
| SEQ ID NO: 1 | 17.4 | increased |
| SEQ ID NO: 2 | 35.8 | increased |
| SEQ ID NO: 3 | 11.4 | increased |
| SEQ ID NO: 4 | 10.1 | increased |
| Hemin | 17.8 | normal |

As shown in Table 1, SEQ ID NO: 1, SEQ ID NO: 2, SEQ ID NO: 3 and SEQ ID NO: 4 induce the synthesis of hemoglobin by K562 cells and an increase in their cell size, two measures of erythroid differentiation.

EXAMPLE 4

Upregulation of Rh D in K562 Cells Cultured with SEQ ID NO: 2 or SEQ ID NO: 3.

The Rh D antigen is the most important antigen of the Rh blood group system. In humans, the Rh D antigen is expressed solely on erythrocytes (Cartron, Blood Rev. 6:199, 1994). K562 cells were seeded in 1.0 ml at $2.0\times10^5$ cells/ml in 6-well flat-bottomed tissue culture plates for 72 hours with 2.5, 10.0, 25.0, 50.0 or 100.0 µg of SEQ ID NO: 2 or SEQ ID NO: 3. The expression of Rh D at the cell surface was monitored by flow cytometry. After incubation, K562 cells were washed twice by centrifugation with PBS and labeled with phycoerythrin (PE)-conjugated anti-Rh D monoclonal antibody (IBGRL research product, Bristol, Netherlands) for 30 min at 4° C. After washing twice with PBS-1% bovine serum albumin, cellular fluorescence was then determined. Flow cytometry was carried out on a FACSCalibur cell sorter (Becton Dickinson, San Jose, Calif., USA) and analyzed using the program CELLQuest (Becton Dickinson). The fold increase in Rh D level over control (0 µg oligonucleotide) was determined. Untreated K562 cells were essentially negative for this marker.

TABLE 2

Fold increase in Rh D level over control in treated K562 with SEQ ID NO: 2 and SEQ ID NO: 3

| SEQUENCE | Concentration (µg/ml) | | | | |
|---|---|---|---|---|---|
| | 2.5 | 10 | 25 | 50 | 100 |
| SEQ ID NO: 2 | 1.7 x | 2.5 x | 4.6 x | 9.8 x | 15.4 x |
| SEQ ID NO: 3 | 2.0 x | 2.2 x | 2.9 x | 6.5 x | 4.7 x |

As shown in Table 2, SEQ ID NO: 2 and SEQ ID NO: 3 induced the expression of Rh D antigen at the cell surface of K562, a measure of erythroid differentiation.

EXAMPLE 5

Upregulation of CD41a Antigen in K562 Cells Cultured with SEQ ID NO: 2 or SEQ ID NO: 3.

The CD41a antigen, also named GpIIb/IIIa, is expressed on platelets and megakaryocytes (Gruel et al., Blood 68:488, 1986). K562 cells were seeded in 1.0 ml at $2.0\times10^5$ cells/ml in 6-well flat-bottomed tissue culture plates for 72 hours with 2.5, 10.0, 25.0, 50.0 or 100.0 µg of SEQ ID NO: 2 or SEQ ID NO: 3. The expression of CD41a at the cell surface was monitored by flow cytometry. After incubation, K562 cells were washed twice by centrifugation with PBS and labeled with phycoerythrin (PE)-conjugated anti-CD41a monoclonal antibody (BD Pharmingen, Mississauga, Ontario, Canada) for 30 min at 4° C. After washing twice with PBS-1% bovine serum albumin, cellular fluorescence was then determined. Flow cytometry was carried out on a FACSCalibur cell sorter (Becton Dickinson) and analyzed using the program CELLQuest (Becton Dickinson). The fold increase in CD41a level over control (0 µg oligonucleotide) was determined. Untreated K562 cells were essentially negative for this marker.

TABLE 3

Fold increase in CD41a level over control in treated K562 cells with SEQ ID NO: 2 or SEQ ID NO: 3

| SEQUENCE | Concentration (µg/ml) | | | | |
|---|---|---|---|---|---|
| | 2.5 | 10 | 25 | 50 | 100 |
| SEQ ID NO: 2 | 3.0 x | 3.9 x | 12.3 x | 20.6 x | 18.9 x |
| SEQ ID NO: 3 | 3.2 x | 3.7 x | 8.3 x | 13.4 x | 11.7 x |

As shown in Table 3, SEQ ID NO: 2 and SEQ ID NO: 3 induced the expression of CD41a antigen, a measure of megakaryocyte differentiation, at the cell surface of K562 cells.

EXAMPLE 6

Upregulation of CD14 in K562 Cells Cultured with SEQ ID NO: 2 or SEQ ID NO: 3.

The CD14 antigen is expressed at high levels on monocytes. Additionally, CD14 is expressed on interfollicular macrophages, reticular dendritic cells and some Langherans cells (Wright et al., Science 249:1434, 1990). K562 cells were seeded in 1.0 ml at $2.0\times10^5$ cells/ml in 6-well flat-bottomed tissue culture plates for 72 hours with 2.5, 10.0, 25.0, 50.0 or 100.0 µg of SEQ ID NO: 2 or SEQ ID NO: 3. The expression of CD14 at the cell surface was monitored by flow cytometry. After incubation, K562 cells were washed twice by centrifugation with PBS and labeled with fluorescein isothiocyanate (FITC)-conjugated anti-CD14 monoclonal antibody (BD Pharmingen) for 30 min at 4° C. After washing twice with PBS-1% bovine serum albumin, cellular fluorescence was then determined. Flow cytometry was carried out on a FACSCalibur cell sorter (Becton Dickinson) and analyzed using the program CELLQuest (Becton Dickinson). The fold increase in CD14 level over control (0 µg oligonucleotide) was determined. Untreated K562 cells were essentially negative for this marker.

TABLE 4

Fold increase in CD14 level over control in K562 cells treated with SEQ ID NO: 2 or SEQ ID NO: 3

| SEQUENCE | Concentration (µg/ml) | | | | |
|---|---|---|---|---|---|
| | 2.5 | 10 | 25 | 50 | 100 |
| SEQ ID NO: 2 | 1.8 x | 1.9 x | 3.9 x | 7.2 x | 9.8 x |
| SEQ ID NO: 3 | 1.9 x | 2.8 x | 3.8 x | 7.2 x | 3.7 x |

As shown in Table 4, SEQ ID NO: 2 and SEQ ID NO: 3 induced the expression of CD14 antigen, a measure of monocyte differentiation, at the cell surface of K562 cells.

EXAMPLE 7

Induction of CD14+ Rh D+, CD14+ CD41a+ and Rh D+ CD41a+Phenotype in K562 Cells Cultured with SEQ ID NO: 2.

K562 cells were seeded in 1.0 ml at $2.0\times10^5$ cells/ml in 6-well flat-bottomed tissue culture plates for 72 hours with 2.5, 10.0, 25.0, 50.0 or 100.0 µg of SEQ ID NO: 2. The expression of CD14, CD41a and Rh D at the cell surface was monitored by two dimensional flow cytometry. After incubation, K562 cells were washed twice by centrifugation with PBS and labeled with FITC-conjugated anti-CD14, PE-conjugated anti-CD41a and/or PE-conjugated anti-Rh D monoclonal antibody (BD Pharmingen) for 30 min at 4° C.

After washing twice with PBS-1% bovine serum albumin, cellular fluorescence was determined. Flow cytometry was carried out on a FACSCalibur cell sorter (Becton Dickinson) and analyzed using the program CELLQuest (Becton Dickinson). The fold increase in CD14$^+$Rh D$^+$, CD14$^+$CD41a$^+$ and Rh D$^+$CD41a$^+$ level over control (0 µg oligonucleotide) was determined. Untreated K562 cells were essentially negative for these markers.

TABLE 5

Fold increase in CD14$^+$Rh D$^+$, CD14$^+$CD41a$^+$ and Rh D$^+$CD41a$^+$ levels in K562 treated with SEQ ID NO: 2

| | Concentration (µg/ml) | | | | |
|---|---|---|---|---|---|
| PHENOTYPE | 2.5 | 10 | 25 | 50 | 100 |
| CD14$^+$Rh D$^+$ | 4.0 x | 7.0 x | 16.0 x | 34.0 x | 41.0 x |
| CD14$^+$CD41a$^+$ | 2.0 x | 2.0 x | 4.0 x | 11.0 x | 22.0 x |
| Rh D$^+$CD41a$^+$ | 20.0 x | 22.0 x | 45.0 x | 87.0 x | 100.7 x |

As shown in Table 5, SEQ ID NO: 2 induced the differentiation of K562 cells into cells with heterogeneous phenotypes.

EXAMPLE 8

Induction of CD14$^+$Rh D$^+$, CD14$^+$CD41a$^+$ and Rh D$^+$CD41a$^+$ Cells Cultured with SEQ ID NO: 3.

K562 cells were seeded in 1.0 ml at 2.0×10$^5$ cells/ml in 6-well flat-bottomed tissue culture plates for 72 hours with 2.5, 10.0, 25.0, 50.0 or 100.0 µg of SEQ ID NO: 3. The expression of CD14, CD41a and Rh D at the cell surface was monitored by two dimensional flow cytometry. After incubation, K562 cells were washed twice by centrifugation with PBS and labeled with FITC-conjugated anti-CD14, PE-conjugated anti-CD41a and/or PE-conjugated anti-Rh D monoclonal antibody (BD Pharmingen) for 30 min at 4° C. After washing twice with PBS-1% bovine serum albumin, cellular fluorescence was then determined. Flow cytometry was carried out on a FACSCalibur cell sorter (Becton Dickinson) and analyzed using the program CELLQuest (Becton Dickinson). The fold increase in CD14$^+$Rh D$^+$, CD14$^+$CD41a$^+$ and Rh D$^+$ CD41a$^+$ level over control (0 µg oligonucleotide) was determined. Untreated K562 cells were essentially negative for these markers.

TABLE 6

Fold increase in CD14$^+$Rh D$^+$, CD14$^+$CD41a$^+$ and Rh D$^+$CD41a$^+$ levels in K562 treated with SEQ ID NO: 3

| | Concentration (µg/ml) | | | | |
|---|---|---|---|---|---|
| PHENOTYPE | 2.5 | 10 | 25 | 50 | 100 |
| CD14$^+$Rh D$^+$ | 7.0 x | 8.0 x | 9.0 x | 11.0 x | 10.0 x |
| CD14$^+$CD41a$^+$ | 2.0 x | 3.0 x | 4.0 x | 4.0 x | 3.0 x |
| Rh D$^+$CD41a$^+$ | 6.0 x | 4.0 x | 7.0 x | 29.0 x | 31.0 x |

As shown in Table 6, SEQ ID NO: 3 induced the differentiation of K562 cells into cells with heterogeneous phenotypes.

EXAMPLE 9

Inhibition of K562 Cell Growth by SEQ ID NO: 2 and SEQ ID NO: 3.

Terminal differentiation of K562 cells has been reported to stop their cellular growth (Bianchi et al., Biochem. Pharmacol. 60:31, 2000). K562 cells were seeded in 1.0 ml at 2.0×10$^5$ cells/ml in 6-well flat-bottomed tissue culture plates for 72 hours with 1.0, 10.0 or 100.0 µg of SEQ D NO: 2 or SEQ ID NO: 3. Cells were counted after 24, 48 and 72 hours of incubation using light microscopy and trypan blue dye.

TABLE 7

Number of K562 cells (× 10$^5$) after treatment with SEQ ID NO: 2 or SEQ ID NO: 3

| | | SEQ ID NO: 2 | | | SEQ ID NO: 3 | | |
|---|---|---|---|---|---|---|---|
| Hours | No oligonucleotide | 1.0 µg/ml | 10.0 µg/ml | 100.0 µg/ml | 1.0 µg/ml | 10.0 µg/ml | 100.0 µg/ml |
| 24 | 3.6 | 3.1 | 2.5 | 2.6 | 3.3 | 2.7 | 3.2 |
| 48 | 7.4 | 7.8 | 6.4 | 2.2 | 8.4 | 7.1 | 3.4 |
| 72 | 11.5 | 11.3 | 8.5 | 1.7 | 11.2 | 8.4 | 3.3 |

As shown in Table 7, SEQ ID NO: 2 and SEQ ID NO: 3 inhibited the cellular growth of K562 cells in a dose-dependent manner. The trypan blue exclusion assay demonstrated that treatment of K562 cells with SEQ ID NO: 2 or SEQ ID NO: 3 was not cytotoxic since no trypan blue dye was incorporated by K562 cells.

EXAMPLE 10

Differentiation of Human Committed Erythroid Precursor by SEQ ID NO: 2

Glycophorin A is the major glycoprotein of the human erythrocyte membrane. Maturation of committed human erythroid precursors is characterized by the expression of glycophorin A at the cell surface and by an increase in intracellular granulosity (Daniel and Greens, Vox Sang. S2:149, 2000; Wheater et al., Functional Histology, a text and color atlas, 2$^{nd}$ edition, Churchill Livingstone, U.K., 1987). Human committed erythroid precursors defined by the cell surface glycoprotein CD36 were isolated from expanded human cord blood CD34+ progenitors by positive immunoselection of CD36+ cells (Clonetics, San Diego, Calif., USA). Human committed erythroid cells were seeded in 1.0 ml at 1.5×10$^5$ cells/ml in 6-well flat-bottomed tissue culture plates for 96 hours with 100.0 µg of SEQ ID NO: 2 or SEQ ID NO: 3. The expression of glycophorin A at the cell surface and the intracellular granulosity were monitored by flow cytometry. After 48 and 96 hours of incubation, human committed erythroid cells were washed twice by centrifugation with PBS and labeled with PE-conjugated glycophorin A monoclonal antibody (Caltag Laboratories, Burlingame, Calif., USA) for 30 min at 4° C. After washing twice with PBS-1% bovine serum albumin, cellular fluorescence was determined. The intracellular granulosity was determined by the measure of side light scatter (SSC) using a flow cytometer. Flow cytometry was carried out on a FACSCalibur (Becton Dickinson) and analyzed using the program CELLQuest (Becton Dickinson). The percentages of cells in SSC$^{hi}$ glycophorin A$^+$ and in SSC$^{lo}$ glycophorin A$^+$ were determined. SSC$^{hi}$ is defined as >450 units; SSC$^{lo}$ is defined as <450 units.

TABLE 8

Percentages of human committed erythroid precursor cells in SSC$^{hi}$ glycophorin A$^+$ and in SSC$^{lo}$ glycophorin A$^+$ after treatment with SEQ ID NO: 2 or SEQ ID NO: 3

| | None | | SEQ ID NO: 2 | | SEQ ID NO: 3 | |
|---|---|---|---|---|---|---|
| | 48 h | 96 h | 48 h | 96 h | 48 h | 96 h |
| SSC$^{hi}$ glycophorinA$^+$ | 0.9 | 1.2 | 8.0 | 12.8 | 0.6 | 0.4 |
| SSC$^{lo}$ glycophorinA$^+$ | 9.1 | 3.8 | 9.3 | 18.1 | 7.4 | 2.2 |

TABLE 8-continued

Percentages of human committed erythroid precursor cells in SSC$^{hi}$ glycophorin A$^+$ and in SSC$^{lo}$ glycophorin A$^+$ after treatment with SEQ ID NO: 2 or SEQ ID NO: 3

|  | None | | SEQ ID NO: 2 | | SEQ ID NO: 3 | |
| --- | --- | --- | --- | --- | --- | --- |
|  | 48 h | 96 h | 48 h | 96 h | 48 h | 96 h |

As shown in Table 8, SEQ ID NO: 2 induced the differentiation of human committed erythroid precursor cells in SSC$^{hi}$ glycophorin A$^+$ and in SSC$^{lo}$ glycophorin A$^+$ cells.

EXAMPLE 11

Effect of SEQ ID NO: 2 on Human Disseminated Chronic Myeloid Leukemia K562 Cells in Severe Combined Immunodeficiency Mice Forty female severe combined immunodeficiency mice (SCID mice) were exposed to 1.8 Gy of radiation (rate: 7.5 Gy/h) from a γ source. Twenty-four hours after whole body irradiation (day 0), the 40 female SCID mice were weighed and randomized to form 4 groups (10 mice/group). The mean body weight of each group was not statistically different from the others (analysis of variance). Mice were injected intraperitoneally (ip) with 2.0×10$^7$ K562 cells in 0.5 ml of RPMI-1640 medium. SEQ ID NO: 2 (5'GGGTGG3') resuspended in 0.9% sodium chloride USP was administrated ip at 0.01, 0.1 and 1 mg per mouse per day from day 1 to day 29 (30 days). A vehicle group was ip injected with vehicle (0.9% sodium chloride USP) following the same schedule. The treatment schedule is summarized in the table below:

TABLE 9

| Group | Treatment | Mice/ group | Route Admin. | Dose/inj. (mg/mouse/ inj.) | Vol./inj. (ml) | Treatment schedule |
| --- | --- | --- | --- | --- | --- | --- |
| 1 | Vehicle | 10 | ip | 0 | 0.250 | Q1DX30 |
| 2 | SEQ ID NO: 2 | 10 | ip | 0.01 | 0.250 | Q1DX30 |
| 3 | SEQ ID NO: 2 | 10 | ip | 0.1 | 0.250 | Q1DX30 |
| 4 | SEQ ID NO: 2 | 10 | ip | 1 | 0.250 | Q1DX30 |

The experiment was stopped at 120 days when mice were sacrificed. Survival was recorded two times per week.

The test evaluation expressed as a percentage (T/C %) and as the increased life span value (ILS %) of the control evaluation was determined. These are measures of the effectiveness of the compounds tested. Survival systems indicate a degree of success when T/C percentages exceed 125 and ILS percentages exceed 25. T is the median survival times of animals treated with drugs and C is the median survival time of control animals. T/C % and ILS % is expressed as following:

$$ILS\% = [(T-C)/C] \times 100$$

$$T/C\% = [T/C] \times 100$$

Statistical analysis was performed using StatView® (Abacus Concept, Berkeley, USA). Statistical analysis of the efficiency of the treatment was performed using the Bonferroni/Dunn test (ANOVA comparison).

TABLE 10

Survival time of SCID mice having human disseminated chronic myeloid K562 leukemia treated with SEQ ID NO: 2

| | TREATMENT | | | |
| --- | --- | --- | --- | --- |
| | Group 1: vehicle Survival time (days) | Group 2: 0.01 mg SEQ ID NO: 2 Survival time (days) | Group 3: 0.1 mg SEQ ID NO: 2 Survival time (days) | Group 4: 1 mg SEQ ID NO: 2 Survival time (days) |
| | 38 | 120 | 85 | 49 |
| | 54 | 57 | 34 | 120 |
| | 46 | 54 | 57 | 41 |
| | 54 | 75 | 75 | 57 |
| | 34 | 120 | 34 | 57 |
| | 38 | 120 | 31 | 99 |
| | 34 | 120 | 64 | 61 |
| | 54 | 61 | 54 | 61 |
| | 75 | 61 | 64 | 46 |
| | 54 | 34 | 41 | 46 |
| | 34 | 38 | 34 | 49 |
| Mean ± sd | 48.6 ± 12.2 | 78.2 ± 34.9 | 52.1 ± 18.7 | 62.4 ± 24.6 |
| median | 46 | 61 | 41 | 49 |
| ILS % | — | 32.6 | −12.2 | 6.5 |
| T/C % | — | 132.6 | 89.1 | 106.5 |

As shown in Table 10, SEQ ID NO: 2, at 0.01 mg/mouse/day, significantly increased the life span of SCID mice having human disseminated chronic myeloid K562 leukemia (p>0.05). After 120 days, 4 of 11 mice treated with SEQ ID NO: 2 at 0.01 mg/mouse/day were alive while none of the 11 untreated mice was alive.

EXAMPLE 12

Effect of SEQ ID NO: 1, SEQ ID NO: 2, SEQ ID NO: 3 and SEQ ID NO: 4 on Differentiation of Bone Marrow-Derived Cells from Mice The C57BL/6 mice are divided into 5 groups of 10 mice. Mice receive gamma-irradiation to induce a reduction in the number of bone marrow derived-cells and bone marrow precursor cells. On day 0, group 1 mice receive saline, group 2 receive SEQ ID NO: 1, group 3 receive SEQ ID NO: 2, group 4 receive SEQ ID NO: 3, group 5 receive SEQ ID NO: 4. Sequences resuspended in 0.9% sodium chloride USP are administrated ip at 0.01 mg per mouse per day for 7 days.

After 7 days of treatment, the mice are sacrificed. Cells present in peripheral blood and in bone marrow are counted and their phenotype determined by flow cytometry. Hemoglobin levels are also determined. Mice in groups 2, 3, 4 and 5 have more bone marrow-derived cells than the mice in group 1. Mice in groups 2, 3, 4 and 5 have more mature bone marrow-derived cells than the mice in group 1. The levels of hemoglobin are more elevated in mice in groups 2, 3, 4 than in mice in group 1.

EXAMPLE 13

Effect of SEQ ID NO: 1, SEQ ID NO: 2, SEQ ID NO: 3 and SEQ ID NO: 4 on CML in SCID Mice K562 cells (2×10$^7$ cells) are inoculated into SCID mice (severe combined immunodeficiency mice) as previously described (Beran et al., Hematol. Pathol. 8:135, 1994). The mice are divided into 5 groups of 10 mice. On day 0, group 1 mice receive saline, group 2 mice receive SEQ ID NO: 1, group 3 mice receive SEQ ID NO: 2, group 4 receive SEQ ID NO: 3, group 5 mice receive SEQ ID NO: 4. Sequences resuspended in 0.9% sodium chloride USP are administrated ip at 0.01 mg per mouse per day for 30 days.

After 30 days, the mice are sacrificed. Leukemic dissemination, leukemic cell phenotype and hemoglobin levels are analyzed. Mice in Group 1 have the most leukemia cells and dissemination. Mice in groups 2, 3, 4 and 5 have less leukemia cells and dissemination. Mice in groups 2, 3, 4 and 5 show a higher number of differentiated K562 cells than mice in group 1. Mice in groups 2, 3, 4 and 5 show more hemoglobin synthesis than the mice in group 1.

All patents, publications and abstracts cited above are incorporated herein by reference in their entirety. It should be understood that the foregoing relates only to preferred embodiments of the present invention and that numerous modifications or alterations may be made therein without departing from the spirit and the scope of the present invention as defined in the following claims.

We claim:

1. A method comprising administration of an amount of a composition comprising an isolated 3'-OH, 5'-OH, chemically unmodified, synthetic phosphodiester nucleotide sequence consisting of a nucleotide sequence, wherein the nucleotide sequence is SEQ ID NO: 1, and a pharmaceutically acceptable carrier, to an animal or a human wherein the amount is effective to induce differentiation of cells in the animal or the human.

2. The method of claim 1, wherein the animal or the human has a disease associated with insufficient differentiation of cells.

3. The method of claim 2, wherein the disease is leukemia, lymphoma, a non-malignant blood disorder, hemoglobinopathy, sickle cell disease, myelodysplastic syndrome, pancytopenia, anemia, thrombocytopenia or leukopenia.

4. The method of claim 2, wherein the disease is leukemia.

5. The method of claim 1, wherein induction of differentiation of cells is induction of erythrocyte-like phenotype, monocyte-like phenotype, megakaryocyte-like phenotype, inhibition of proliferation or induction of hemoglobin synthesis in cells.

6. A method comprising administration of an amount of a composition comprising an isolated 3'-OH, 5'-OH, chemically unmodified, synthetic phosphodiester nucleotide sequence consisting of a nucleotide sequence, wherein the nucleotide sequence is SEQ ID NO: 1, and a pharmaceutically acceptable carrier, to an animal or a human, wherein the amount is effective to increase differentiation of pluripotent cells in the animal or the human.

7. The method of claim 6, wherein the animal or the human has received chemotherapy or radiotherapy.

8. The method of claim 6, further comprising administration of a therapeutic agent.

9. The method of claim 8, wherein the therapeutic agent is a chemotherapeutic drug, an immunosuppressive agent, a differentiating agent, an immunotherapeutic agent, an antimicrobial agent, an antiviral agent, radiotherapy, or a combination thereof.

10. The method of claim 6, wherein the pluripotent cells are derived from bone marrow, liver, spleen, lymph nodes, thymus or cord blood.

11. The method of claim 6, wherein the pluripotent cells are derived from bone marrow.

12. A method comprising administration of an amount of a composition comprising an isolated 3'-OH, 5'-OH, chemically unmodified, synthetic phosphodiester nucleotide sequence consisting of a nucleotide sequence, wherein the nucleotide sequence is SEQ ID NO: 1, and a pharmaceutically acceptable carrier, to an animal or a human having a disease associated with insufficient differentiation of cells, wherein the amount is effective to induce differentiation of cells in the animal or the human.

13. The method of claim 12, wherein the disease is leukemia and the amount is effective to treat the leukemia.

* * * * *

SEQUENCE LISTING

```
<160> NUMBER OF SEQ ID NOS: 5

<210> SEQ ID NO 1
<211> LENGTH: 3
<212> TYPE: DNA
<213> ORGANISM: Artificial Sequence
<220> FEATURE:
<223> OTHER INFORMATION: synthetic oligonucleotide

<400> SEQUENCE: 1 gtg                                                                     3

<210> SEQ ID NO 2
<211> LENGTH: 6
<212> TYPE: DNA
<213> ORGANISM: Artificial Sequence
<220> FEATURE:
<223> OTHER INFORMATION: synthetic oligonucleotide

<400> SEQUENCE: 2 gggtgg                                                                  6

<210> SEQ ID NO 3
<211> LENGTH: 6
<212> TYPE: DNA
<213> ORGANISM: Artificial Sequence
<220> FEATURE:
<223> OTHER INFORMATION: synthetic oligonucleotide

<400> SEQUENCE: 3 gggagg                                                                  6

<210> SEQ ID NO 4
<211> LENGTH: 6
<212> TYPE: DNA
<213> ORGANISM: Artificial Sequence
<220> FEATURE:
<223> OTHER INFORMATION: synthetic oligonucleotide

<400> SEQUENCE: 4 ccaccc                                                                  6

<210> SEQ ID NO 5
<211> LENGTH: 5
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (3)..(5)
<223> OTHER INFORMATION: Any "n" = any nucleotide

<400> SEQUENCE: 5 cgnnn                                                                   5
```